United States Patent [19]
Towlen

[11] Patent Number: 5,832,926
[45] Date of Patent: Nov. 10, 1998

[54] HEAD SUPPORT DEVICE

[76] Inventor: Paul Raymond Towlen, 30 Berkshire Heights Rd., Great Barrington, Mass. 01230

[21] Appl. No.: 578,963

[22] Filed: Dec. 27, 1995

[51] Int. Cl.$^6$ .................................................. A61G 15/00
[52] U.S. Cl. ............................... 128/845; 602/17; 602/19
[58] Field of Search .................................... 128/845, 846, 128/857, 858; 602/17, 18, 19; 2/2, 425; 606/130

[56] References Cited

U.S. PATENT DOCUMENTS

| | | |
|---|---|---|
| 1,179,063 | 4/1916 | Aldrete . |
| 1,803,556 | 5/1931 | Nugent . |
| 2,583,803 | 1/1952 | Amer . |
| 2,598,291 | 5/1952 | O'Brien . |
| 3,359,976 | 12/1967 | Laval ........................................ 602/17 |
| 3,697,065 | 10/1972 | Glassburrer .............................. 602/17 |
| 3,957,040 | 5/1976 | Calabrese . |
| 4,161,946 | 7/1979 | Zuesse . |
| 4,732,144 | 3/1988 | Cunanan .................................. 602/18 |
| 4,951,655 | 8/1990 | MacMillan et al. . |
| 5,020,897 | 6/1991 | Frye . |
| 5,203,765 | 4/1993 | Friddle ..................................... 602/17 |
| 5,242,377 | 9/1993 | Boughner et al. . |
| 5,261,125 | 11/1993 | Cartwright ............................... 602/17 |
| 5,302,170 | 4/1994 | Tweardy . |

OTHER PUBLICATIONS

Kelly, N.E., Wendel, R.T., "Vitreous Surgery for Idiopathic Macular Holes Results of a Pilot Study", *Arch Ophthalmol*, pp. 654–659, May, 1991, Believed to be U.S.A.

Wendel, R.T., Patel, A.C., Kelly, N.E., Salzano, T.C., Wells, J.W., Novack, G.D., "Vitreous Surgery for Macular Holes", *Opthalmology*, pp. 1671–1676, Nov., 1993, Believed to be U.S.A.

Gass, J.D.M., "Idiopathic Senile Macular Hole Its Early Stages and Pathogenesis", *Arch Ophthalmol*, pp. 629–639, May, 1988, Believed to be U.S.A.

Johnson, R.N., Gass, J.D.M., "Idiopathic Macular Holes Observations, Stages of Formation, and Implications for Surgical Intervention", *Ophthalmology*, pp. 917–924, Jul., 1988, Believed to be U.S.A.

*Primary Examiner*—Michael A. Brown
*Attorney, Agent, or Firm*—Abelman, Frayne & Schwab

[57] ABSTRACT

A device for restraining and supporting the head of a user at a given forward angle while alleviating resultant neck, shoulder, and back pain comprises an angularly adjustable upper section contacting the head of a user, a fixed intermediate section for transmitting the force applied by the head of a user to the device to the user's upper back and shoulders, and a lower section contacting the lower back of a user. The device is attached to the body of a user by a back support belt. The device may optionally support a removable mirror from its upper section to enable a user to view his or her surroundings while the user's head is restrained and supported by the device.

20 Claims, 8 Drawing Sheets

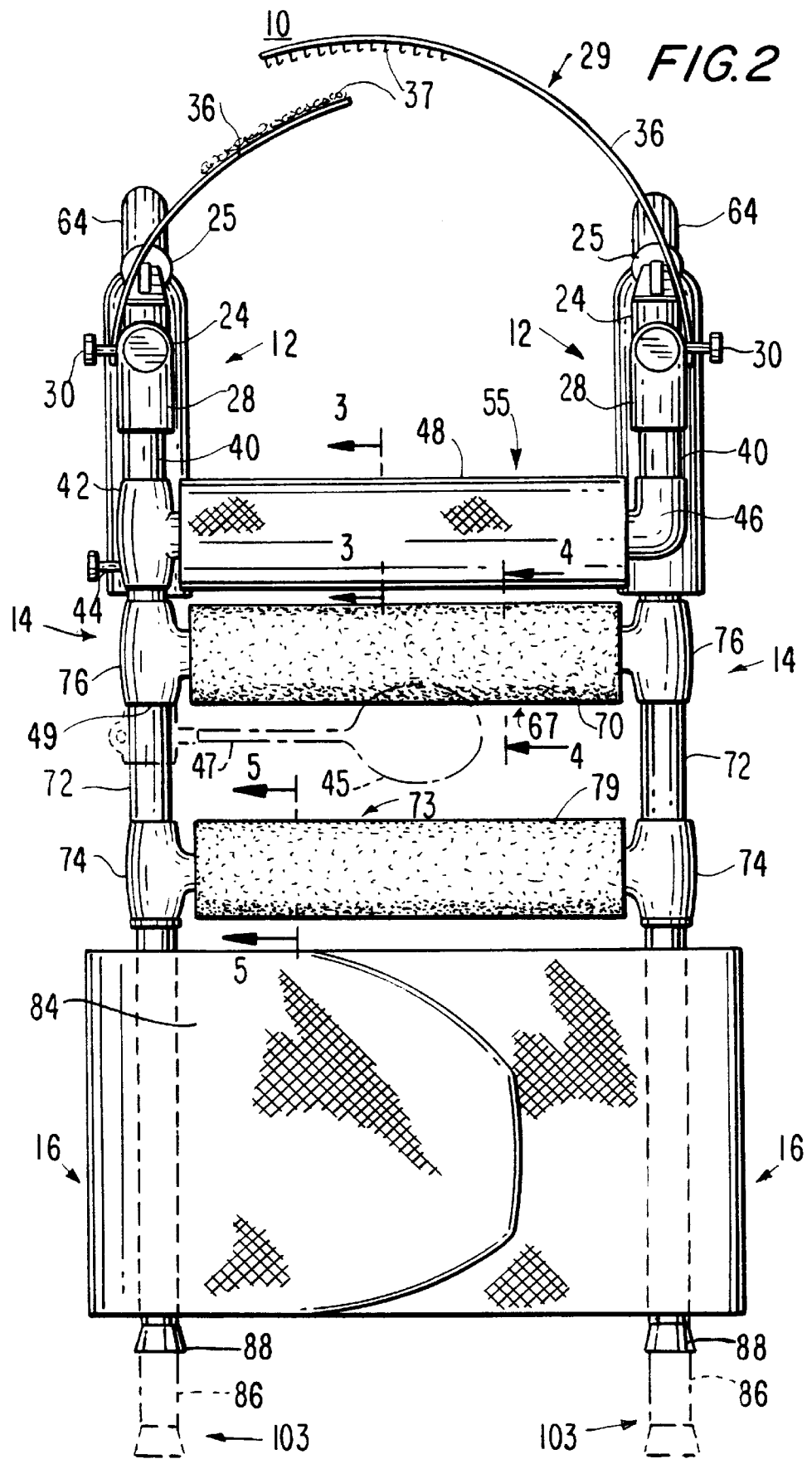

HEAD SUPPORT DEVICE

BACKGROUND OF THE INVENTION

1. Field of the Invention

This invention relates to the stabilizing devices to be worn by individuals after surgery or in other situations and, more particularly, to head supports and restraints to fix the head of a person during healing after vitrectomy surgery or in other situations.

2. Description of the Related Art

In certain persons, a hole develops in the macula lutea retinae, a depression on the retina. Retinal detachment around the rim of the macular hole from the underlying retinal pigment epithelium and a loss of visual acuity is associated with the macular hole. Until recently thought untreatable, macular holes are now treated with eye surgery comprising pars plana vitrectomy, removing any cortical portions of the vitreous body of the eye adhering to the retina and any epiretinal membranes, and a total gas-fluid exchange (the eye surgery hereinafter being referred to as "vitrectomy" for the sake of brevity). At the end of surgery, sulfur hexaflouride gas is injected to lengthen intraocular tamponade.

Vitrectomy attempts to reattach the portion of the retina around the rim of the macular hole. In many of the cases where such reattachment is successfully effected, an improvement in visual acuity has been reported. The head must be held down for a minimum of one week after this surgery according to the relevant medical literature. The information presented herein on macular holes and vitrectomy was drawn from Kelly, N. E., Wendel, R. T., "Vitreous Surgery for Idiopathic Macular Holes Results of a Pilot Studt", *Arch Ophthalmol.* 1991;109:654–659 and Wendel, R. T., Patel, A. C., Kelly, N. E., Salzano, T. C., Wells, J. W., Novack, G. D., "Vitreous Surgery for Macular Holes", *Ophthalmology* 1993;100:1671–1676. Further information on macular holes may be found in Gass, J. D. M., "Idiopathic Senile Macular Hole Its Early Stages and Pathogenesis", *Arch Ophthalmol.* 1988;106:629–639 and Johnson, R. N., Gass, J. D. M., "Idiopathic Macular Holes Observations, Stages of Formation, and Implications for Surgical Intervention", *Ophthalmology* 1988;95:917–924.

Many patients who undergo vitrectomy for this condition of macular hole are elderly and it is difficult for them to keep their heads down for such an extended period of time. In addition, such a position of the head of a patient would be most dangerous while walking since the patient would be unable to see his or her surroundings.

The prior art does not provide a suitable device to keep the head of a person in a selected one of adjustable positions, including a downward position, while alleviating neck, shoulder, and back pain otherwise resulting from keeping the head in such a stabilized position. The prior art is also devoid of suitable stabilizing devices which also allow the user to see his or her surroundings. Furthermore, the prior art does not provide a device which releasably restrains the head in an upright position without engaging the neck of a user, while allowing a user to see his or her surroundings.

There are devices which maintain the head of a user in an upright position by rigid supports for various purposes. A group of devices maintain traction directly against the head in order to immobilize and provide support to the cervical spine area of a patient.

U.S. Pat. No. 3,957,040 to Calabrese, U.S. Pat. No. 4,951,655 to MacMillan et al., and U.S. Pat. No. 5,302,170 to Tweardy, are typical devices from this group.

Calabrese, U.S. Pat. No. 3,957,040, discloses a cervical brace comprising a shoulder embracing portion fitted to cover both shoulders of a person and a curved head engaging portion for contacting the lower rear of a person's head adjacent the occipital bone with a forehead engaging portion extending therefrom. Three longitudinally adjustable rigid members are pivotably connected between the shoulder and head engaging portions of the brace. Two of these rigid members are connected between each of the shoulder engaging portions over each shoulder of a person and opposite sides of the head engaging portion over opposite sides of a person's head. The third rigid member is connected between the back of the head engaging portion over the back of a person's head and the shoulder engaging portion between the first two rigid members.

MacMillan et al., U.S. Pat. No. 4,951,655, discloses a cervical spine support comprising a vest or other covering for the upper body, a front and rear pair of rigid vertical vest bars, and a hoop encircling the head of a user at the level of a user's mouth. The hoop is secured to the vest bars and carries a maxillary bridge comprising a maxillary tooth splint adapted to engage the upper set of teeth of the wearer and a bridge member attached to and spanning the distance between the hoop and the maxillary tooth splint. Two occipital support pads are attached to the hoop by threaded positioning screws. These screws allow the pads to move into an engaging position with the neck of the user at the occipital bone region at the posterior base of the skull.

Tweardy, U.S. Pat. No. 5,302,170, discloses a device comprising a truncated rigid halo designed to fit around a user's head with the open portion of the halo at the back of the user's head. The halo has holes in it for skull pins to pass through to actually contact and grip the user's head. The device also comprises a rigid support structure for attaching the partial halo to a vest worn by the user. The support structure has both horizontal and vertical rack and pinion adjustments for adjusting the height and angular position of the halo.

Other devices which support the head for miscellaneous purposes are typically disclosed in U.S. Pat. No. 1,803,556 to Nugent, U.S. Pat. No. 4,161,946 to Zuesse, and U.S. Pat. No. 5,242,377 to Boughner et al.

Nugent, U.S. Pat. No. 1,803,556, discloses a device to support the wearer's spinal column. The device comprises a pad worn at the base of the spinal column and an abdominal pad connected together by straps. A pair of vertical threaded rods are attached to the pad at the base of the spinal column and extend upwardly with their ends threadably engaged into two telescoping rods whose upper ends are attached to a pad worn between the shoulders and on the back of a user. A pair of L-shaped rods are attached to the pad between the shoulders of the user and extend over the shoulders of a user, being adjustably attached to side pads fitted over the shoulders of a user and terminating across the chest and back of a user. An L-shaped head bar is adjustably attached to the shoulder pad and extends over the top of the head of the user. A sleeve member is slidable longitudinally on the end of the head bar above the head of the user and supports a head strap and chin strap supporting the head of a user.

Zuesse, U.S. Pat. No. 4,161,946, discloses a support for maintaining the head in an upright position while resting or sleeping so as to facilitate sleeping while traveling in cars, buses, trains, airplanes, or other conveyances. The device comprises two rigid but adjustable parts extending from a structure engaging the nape of the neck of a wearer. The first part is a headband extending forwardly and upwardly from the nape engagement means to engage a user's forehead. The second part extends forwardly and downwardly from the nape engagement means to engage a user's sternum. Alternatively, the device can comprise flexible material having within it an inflatable air chamber to provide semi-rigid support.

Boughner et al., U.S. Pat. No. 5,242,377, discloses a head and neck support device for use by persons having a neck weakened by various conditions resulting in poor head control. The device comprises a first plate secured to the upper torso and a second plate secured to the first plate and extending upward from the first plate to a position behind the head of a user. The second plate is attached by a tethering system to a harness that is worn circumferentially around the head. The head harness comprises a forehead strap and a crown or top strap. The first plate is attached to the body by a torso harness. The curvature of the first and second plate may be varied by a system of turnbuckles.

Devices are also known which support mirrors from the body of a user. Examples of these are U.S. Pat. No. 1,179,063 to Aldrete, U.S. Pat. No. 2,583,803 to Amer, U.S. Pat. No. 2,598,291 to O'Brien, and U.S. Pat. No. 5,020,897 to Frye.

Aldrete, U.S. Pat. No. 1,179,063, discloses a frame adapted to pass over the shoulders and to rest on the chest of a user. A removable wire bracket is attached to the frame which supports a mirror. The mirror's vertical and horizontal position can be adjusted with respect to the body of a user.

Amer, U.S. Pat. No. 2,583,803, discloses a rod-like member passing over the shoulders of a user and supporting a mirror on the two ends of the rod-like member in front of the user. The rod-like member may optionally be divided into a section around the shoulders of the user and arms supporting the mirror swingably connected to the shoulder section in order to vary the angular position of the arms and the mirror. In addition, the arms may themselves frictionally telescope into members actually attached to the mirror to vary the distance of the mirror from the user.

O'Brien, U.S. Pat. No. 2,598,291, discloses a device comprising a belt to be worn about the waist of a user, two vertical members running upwardly along the back of a user from the belt to a horizontal member running between the shoulders of a user. Straps from the horizontal member pass under the armpits of a user to a detachable strap running across the chest of a user. Three mirrors and an illuminating bulb to the rear of the back of a user are supported by a rod-like member disposed in a triangular shaped bracket supported by the belt, the horizontal member, and a horizontal member running between the two vertical members.

Frye, U.S. Pat. No. 5,020,897, discloses a device specifically intended to aid eyedrop medication users and contact lens wearers in the application of eyedrop medication or in placing or removing contact lenses by providing an image of the user's eyes. The device comprises an adjustable headband and a pair of forwardly extending side arms pivotally mounted about a transverse axis on the headband and pivotally supporting a transverse mirror housing and mirror therebetween.

SUMMARY OF THE INVENTION

The present invention is a device which comprises an angularly adjustable upper section which restrains and supports the head of a user in an upright, downward, or intermediate position and optionally allows the user to see his or her surroundings at the same time. The force applied by the head of a user to the upper section is transmitted to a fixed intermediate section of the device which, in turn, transmits the force to the shoulders and upper back of a user. A lower section of the device contacts the lower back of a user through tube legs which may or may not be vertically adjustable. The device is attached to the body of a user through a back support belt worn about the waist area of a user and attached to the tube legs or the fixed intermediate section of the device. The weight of the device is further supported by the body of a user through shoulder strap loops encircling the shoulders of a user and attached to the back support belt.

The device finds particular utility in comfortably maintaining the user's head in a downward position during the healing period following eye vitrectomy surgery. However, such application is only an illustration of a potential use of the invention and is not meant to limit the invention as disclosed since there may be many other uses for the invention. For example, the invention as disclosed herein may be used to hold a user's head in an upright position to straighten or support the user's cervical spine.

It is an object of the present invention to provide a device which restrains and supports a user's head in a desired position while permitting mobility and allowing the user to see the surroundings.

It is a further object of the present invention to allow a user to adjust the angle to the horizontal at which the head is restrained and supported for comfort, medical necessity, or both.

It is a further object of the present invention to provide a supporting device which alleviates neck, back, and shoulder pain otherwise experienced by patients who must keep their heads in a downward position.

It is a further object of the present invention to support the force applied to the device by a user's head by cantilever action of the device transmitting the force applied directly to the user's back and shoulders, thereby largely avoiding such force transmission through the user's neck and alleviating the neck pain of the user.

It is a further object of the invention to distribute and cushion the transmission of force to the user's back and shoulders by the device through the use of padding placed on the device.

These and other objects and advantages of the present invention will become more apparent to those of ordinary skill in the art upon consideration of the attached drawings and the following description of the preferred embodiment which are meant by way of illustration and example only, but are not to be construed as in any way limiting the invention disclosed and claimed herein.

BRIEF DESCRIPTION OF THE DRAWINGS

FIG. 2 is a front elevational view of the head support device looking in the direction of 2—2 in FIG. 1.

DESCRIPTION OF THE PREFERRED EMBODIMENTS

FIGS. 1, 1a, 1b, 1c, and 2 show overall views of a head support device 10. The head support device 10 comprises an upper section 12 which is angularly adjustable and supports the head of a user, an intermediate section 14 which is fixed and contacts the shoulders and upper back of a user, and a lower section 16 which contacts the lower back of a user and is vertically adjustable relative to the lower back of a user.

Figure 1:
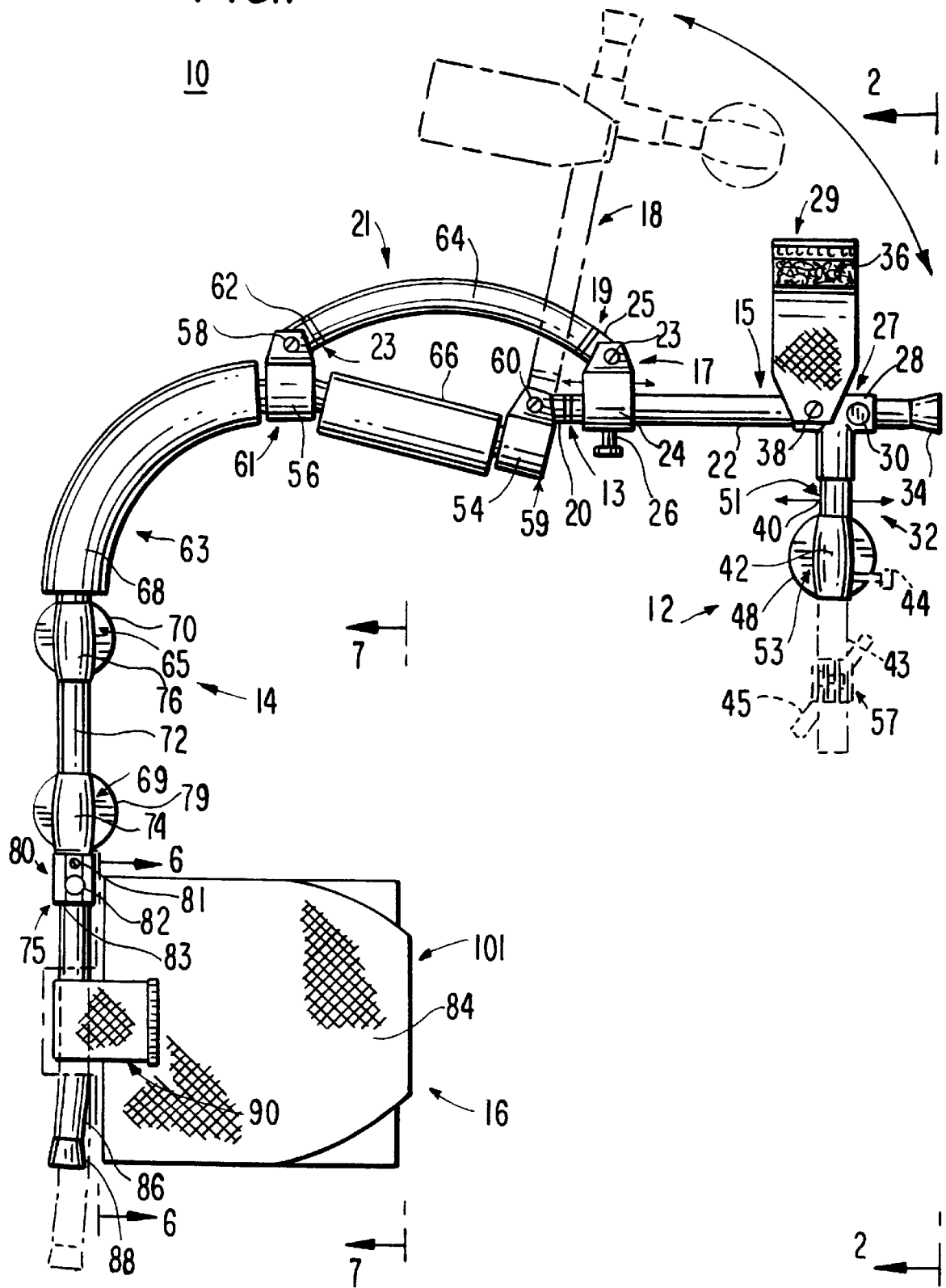
FIG. 1 is an elevational side view of a head support device.
Figure 1A:
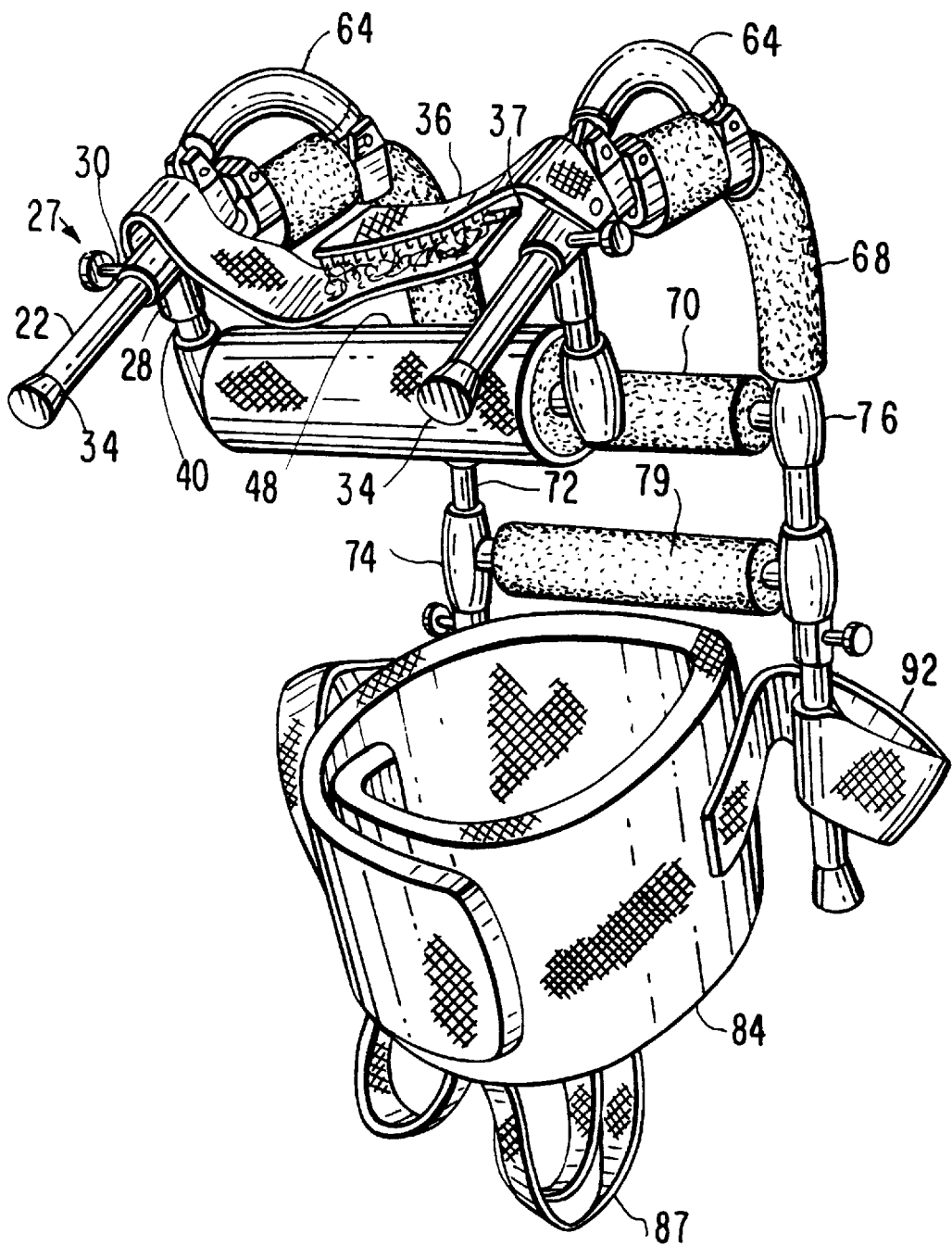
FIG. 1a is a perspective view of a head support device, adjusted as shown in FIG. 1.

The upper section 12 is shown in FIGS. 1, 1a, and 2 in a horizontal position, one of the range of downward positions to which the upper section 12 may be adjusted to support the head of a user. The maximum angle to the horizontal to which the upper section 12 may be adjusted is shown in phantom 18 in FIG. 1. The maximum angular adjustment would allow a user to keep his or her head in an vertical position should that ever become necessary. Of course, it should be appreciated that the range of angular adjustment shown is designed to accomodate the particular position or positions desired by a user as dictated by the user's comfort and the medical necessity for treating the condition of a particular user. Furthermore, it should also be appreciated that the range of angular adjustment shown is by way of illustration only and may vary (see FIG. 1c), depending on the particular embodiment of this invention.

The upper section 12, in turn, comprises, at each side of the head of a user, a first rotatably adjustable attachment means 13, a support means 15, a fixable sliding means 17, a second rotatably adjustable attachment means 19, a rotatably adjustable support means 21, a third rotatably adjustable attachment means 23, a connection means 27, and a releasable head enclosing means 29. Further, the upper section 12 comprises only one head support means 32.

The first rotatably adjustable attachment means 13 preferably comprises an eye end 20 and a fastener 60. The support means 15 preferably comprises a tube 22 and an end cap 34. The fixable sliding means 17 preferably comprises a jaw slide 24 and a set screw 26. The second rotatably adjustable attachment means 19 preferably comprises an eye end 25 and a fastener 23. The rotatably adjustable support means 21 preferably comprises a tube 64. The third rotatably adjustable attachment means 23 preferably comprises an eye end 62 and a fastener 58. The connection means 27 preferably comprises a ninety degree (90°) tee 28 and a set screw 30. The releasable head enclosing means 29 preferably comprises a head strap 36, a head attachment surface 37 (see FIG. 2), and a fastener 38.

The eye end 20 is preferably made of the product polycarbonate sold under the trademark "LEXAN" of the General Electric Company, Pittsfield, Mass. 01201. The jaw slide 24, the eye end 25, and the eye end 62 are also preferably made of "LEXAN". The tubes 22, 64 are preferably made of aluminum to provide light weight and high strength qualities. The tee 28 is also preferably made of aluminum, but may also be made of other materials, such as stainless steel. The set screws 26, 30 and the fasteners 23, 38, 58, 60 are all preferably metallic, except that the set screws 26, 30 each has a plastic cap 27 (see FIG. 1b) on their heads to allow a user to turn the set screws 26, 30 without injury or pain to the user's hands. The end cap 34 is preferably made of plastic, the head strap 36 is preferably made of polypropylene, and the head strap attachment surface 37 is preferably of "VELCRO". Polypropylene head straps can be obtained from Manart Hirsch, 1405 SW 6th Court, Pompano Beach, Fla. 33069. "VELCRO" for the head strap attachment surface 37 can be obtained from ABC Supply Co., 4500 North Dixie Hwy., Ft. Lauderdale, Fla. 33334.

The eye end 20 is attached to and is partially enclosed by a first end of the tube 22. The end cap 34 is attached to and encloses a second end of the tube 22. The jaw slide 24 is attached to the eye end 25 in a manner allowing the rotation of the eye end 25 with respect to the jaw slide 24. The rotatable attachment of the jaw slide 24 to the eye end 25 is accomplished by the fastener 23 rotatably fastening the jaw slide 24 to the eye end 25 (the necessity for such rotatable attachment being explained later). A first end of the tube 64 is attached to and partially encloses the eye end 25 and a second end of the tube 64 is attached to and partially encloses the eye end 62. The tube 22 passes through the tee 28. The tee 28 connects the head support section 32 to the tube 22. The set screw 30 is attached to the tee 28 allowing the releasable setting of the longitudinal position of the tee 28 and the connected head support section 32 along the tube 22, (the necessity for adjusting the longitudinal position being explained later). The tube 22 also passes through the jaw slide 24, an aperture being provided in the jaw slide 24 for this purpose. The set screw 26 is attached to the jaw slide 24 allowing the releasable setting of the longitudinal position of the jaw slide 24 along the tube 22 (the necessity for adjusting the longitudinal position being explained later). The fastener 38 fastens a first end of the head strap 36 to the tee 28. The head strap 36 encloses and restrains the head of a user supported by the head support section 32 and has the head strap attachment surface 37 in the region adjacent to a second end of the head strap 36 as shown in FIG. 2. The head strap attachment surface 37 releasably attaches the head strap 36 to the other head strap 36 on the other side of the head of a user.

The set screw 26 is attached to the jaw slide 24 such that the axis of rotation of the set screw 26 is perpendicular to the axis of the tube 22. The set screw 26 is in contact with the tube 22 when the jaw slide 24 is stationary with respect to the tube 22, thus assuring the stationary position of the jaw slide 24. By rotation of the set screw 26 in the appropriate direction, the set screw 26 is released from contact with the tube 22, and the longitudinal adjustment of the jaw slide 24 with respect to the tube 22 is permitted.

The set screw 30 is attached to the tee 28 such that the axis of rotation of the set screw 30 is perpendicular to the axis of the tube 22 and is in contact with the tube 22 when the tee 28 is stationary with respect to the tube 22, thus assuring the stationary position of the tee 28. The set screw 30, upon being released from contact with the tube 22 by rotation of the set screw 30 in the appropriate direction, allows the longitudinal adjustment of the tee 28 and the attached head support section 32 along and with respect to the tube 22. This longitudinal adjustment allows the head support section 32 to accomodate various users of different sizes whose respective heads will be at varying positions in the horizontal direction with respect to the head support device 10 and, thus, will require the adjustment of the head support section 32 as aforesaid to provide the needed support to their respective heads.

Figure 1B:
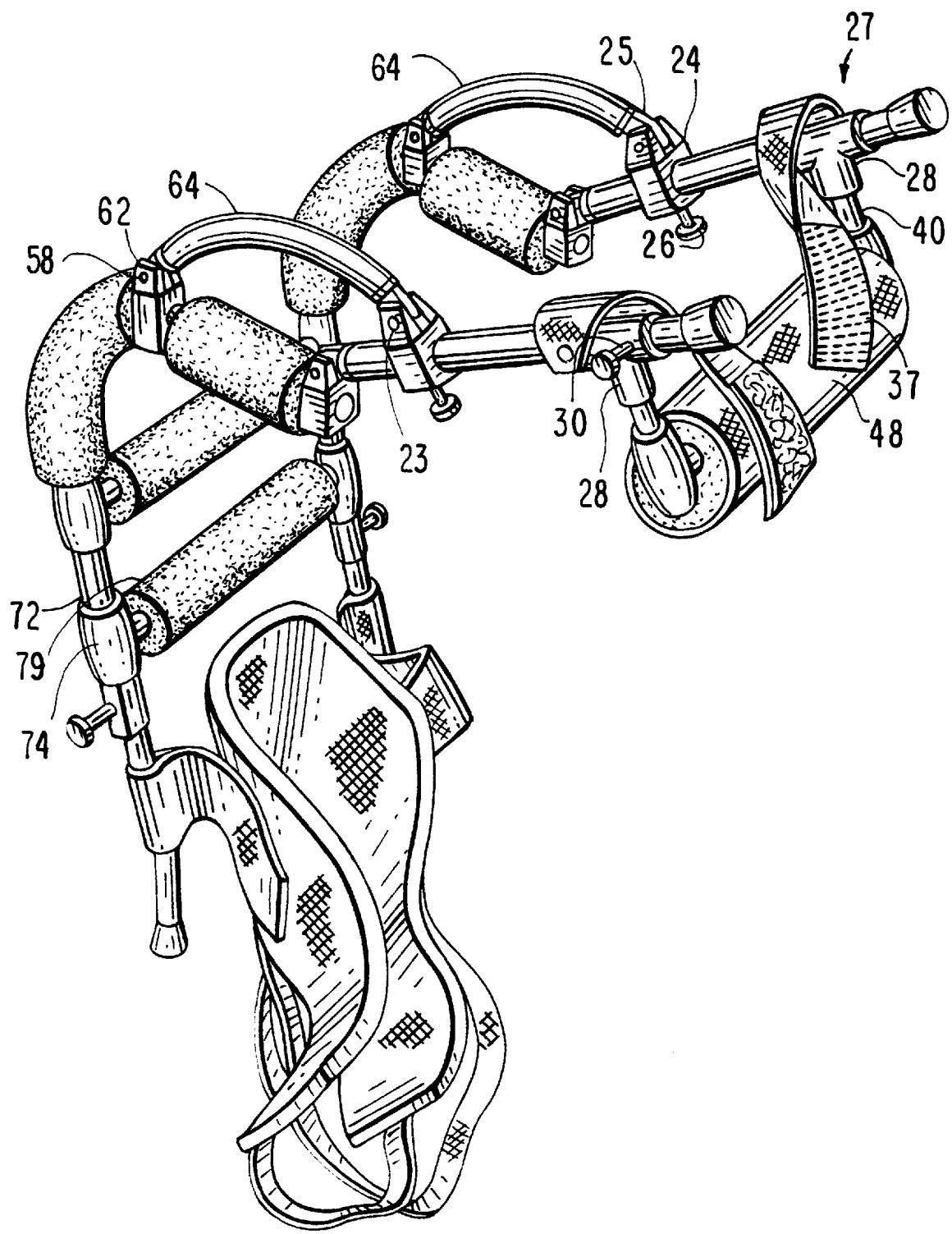
FIG. 1b is a perspective view of a head support device with its upper section fixed at an angle to the horizontal.
Figure 1C:
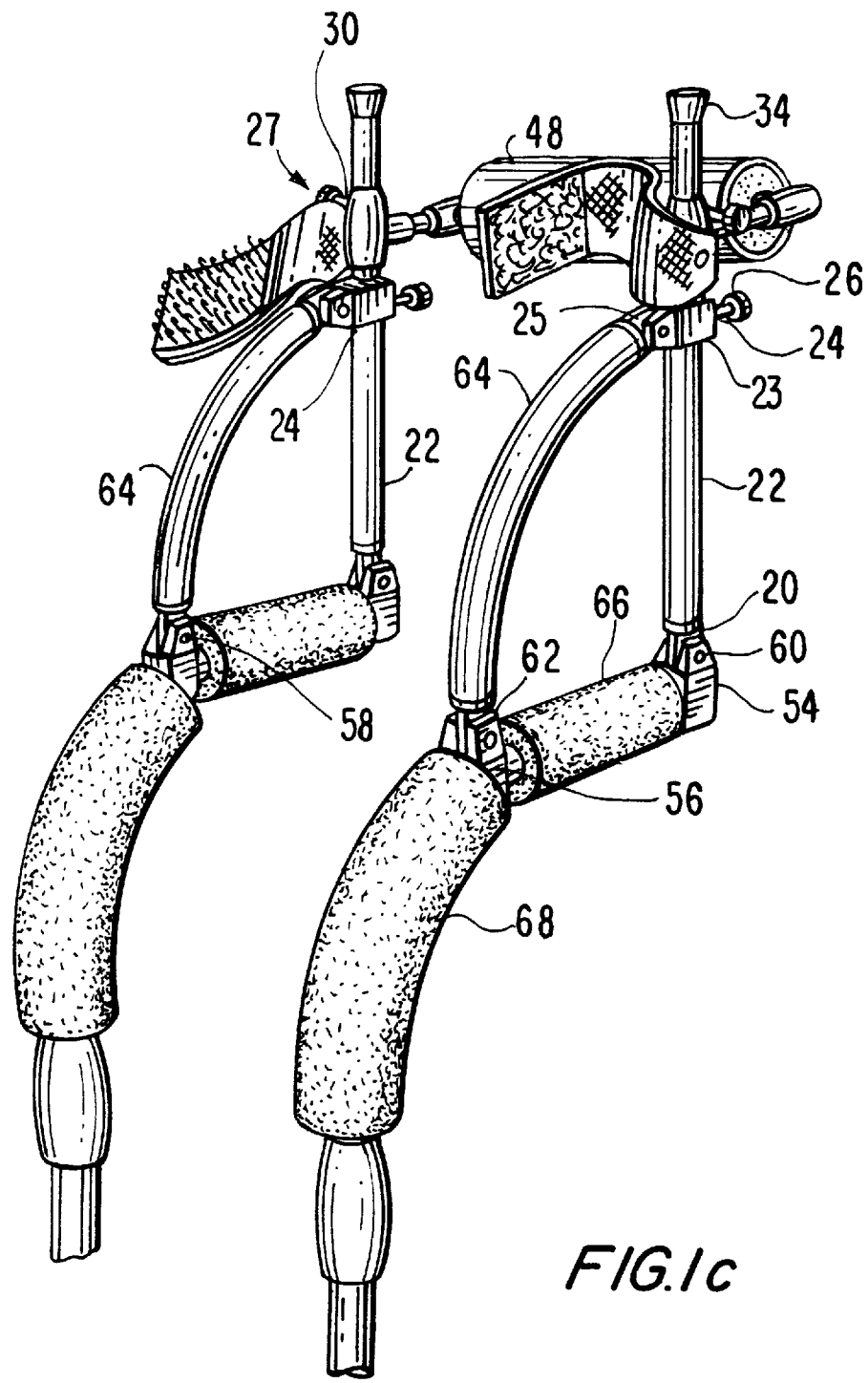
FIG. 1c is a partial perspective view of a head support device with its upper section in an upright position.

Since the tube 64 is of fixed length and remains attached to the eye ends 25, 62 during the angular adjustment of the upper section 12, the jaw slide 24 must be and is longitudinally adjustable along the tube 22 as previously mentioned in order to allow the angular adjustment of the upper section 12. Specifically, as the angle of the upper section 12 is increased with the horizontal, the jaw slide 24 must be longitudinally adjusted with respect to the tube 22 so that the distance between the jaw slide 24 and the end cap 34, measured along the tube 22, is decreased. Conversely, as the angle of the upper section 12 is decreased with the horizontal, the jaw slide 24 must be longitudinally adjusted with respect to the tube 22 so that the distance between the jaw slide 24 and the end cap 34, measured along the tube 22, is increased. An examination of FIG. 1, in conjunction with FIGS. 1b and 1c showing the upper section 12 at an angle to the horizontal and in an upright position, respectively, will greatly aid in understanding this explanation.

It should be noted that the longitudinal position of the tee 28 with respect to the tube 22 will, in some cases, limit the angular adjustment range of the upper section 12 more than in other cases due to the necessity of longitudinally adjusting the jaw slide 24 with respect to the tube 22 in order to effect the angular adjustment as previously explained. Specifically, as can be seen from FIG. 1, the greater the distance from the end cap 34 to the tee 28, measured along the tube 22, the smaller the allowable angular adjustment range of the upper section 12 before the jaw slide 24 contacts the tee 28. Conversely, the smaller the distance from the end cap 34 to the tee 28, measured along the tube 22, the greater the allowable angular adjustment range of the upper section 1 2 before the jaw slide 24 contacts the tee 28.

Figure 3:
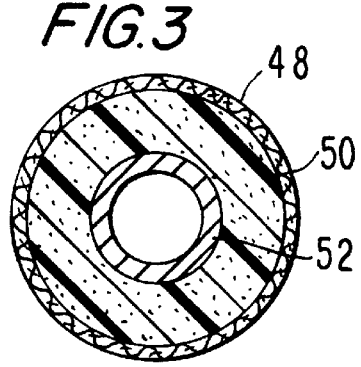
FIG. 3 is a cross-sectional looking in the direction of 3—3 in FIG. 2.

The head support means 32, in turn, comprises two headrest support means 51 preferably comprising two tubes 40, preferably of aluminum, one tube being disposed on each side of the head of a user, a headrest attachment means 53 preferably comprising a ninety degree (90°) tee 42 and a ninety degree (90°) elbow 46 (see FIG. 2), and headrest means 55, (see FIG. 2), preferably comprising a removable cylindrical headrest cover 48, preferably of terrycloth, cylindrical padding 50 for a headrest, preferably of elastomeric pipe insulation sold under the trademark "AP ARMAFLEX" owned by Armstrong World Industries, Inc., Lancaster, Pa. 17604 (see FIG. 3), and a tube 52 serving as the headrest (see FIG. 3), preferably of aluminum. The tee 42 and the elbow 46 are preferably of aluminum, but may be made of stainless steel. The head support device 10 optionally comprises removable viewing means 57 preferably comprising the components shown in phantom on FIGS. 1 and 2: a set screw 44, a hanger tube 43, a collar 49, an adjustable arm 47, and a mirror 45. The set screw 44 is preferably metallic with a plastic cap (not shown) over the head of the set screw 44 to protect a user from injury or pain to the user's hands when turning the set screw 44. The hanger tube 43 is preferably aluminum. The collar 49 and the adjustable arm 47 are preferably of plastic.

One tube 40 is connected at a first end to the tee 28 and at a second end to the tee 42. The other tube 40 is connected at a first end to the tee 28 and at a second end to the elbow 46. The tube 52 is attached at a first end to the tee 42 and at a second end to the elbow 46. The padding 50 covers the tube 52 along substantially the entire length of the tube 52. The headrest cover 48 removably covers the padding 50. The headrest cover 48 is designed to provide as comfortable a surface as possible for the user to rest his or her head for extended periods of time. If for any reason, the user desires to rest his or her head directly on the padding 50, the headrest cover 48 can be removed as aforesaid.

The axis of rotation of the set screw 44, which is optionally attached to the tee 42, is perpendicular to the axis of the tube 40 and the hanger tube 43. The set screw 44 allows a user to fix the hanger tube 43 within the tee 42 by establishing contact between the set screw 44 and the hanger tube 43 or to remove the hanger tube 43 from the tee 42 by breaking contact between the set screw 44 and the hanger tube 43. The collar 49 and the adjustable arm 47 support the mirror 45 by connecting the mirror 45 to the hanger tube 43. The collar 49 encloses a portion of the hanger tube 43 and the adjustable arm 47 is attached at a first end to the collar 49 and at a second end to the mirror 45. The adjustable arm 47 preferably allows limited adjustment of the mirror 45 in the vertical, horizontal, and angular directions, thereby allowing a user to see in a selected direction while a user's head is in position supported by the headrest cover 48 or the padding 50.

The intermediate section 14 comprises two first attachment means 59, two second attachment means 61, two curvilinear upper back and shoulder contact means 63, two first transverse attachment means 65, a first transverse upper back contact means 67, two second transverse attachment means 69, a second transverse upper back contact means 73, and two coupling means 75.

Figure 4:
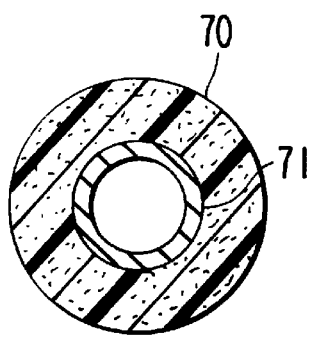
FIG. 4 is a cross-sectional view looking in the direction of 4—4 in FIG. 2.
Figure 5:
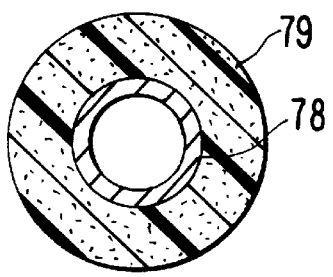
FIG. 5 is a cross-sectional view looking in the direction of 5—5 in FIG. 2.

The first attachment means 59 preferably comprises a fixed jaw slide 54, preferably of "LEXAN", each first attachment means 59 being disposed at a distinct side of the body of a user. The second attachment means 61 preferably comprises a fixed jaw slide 56, preferably of "LEXAN", each second attachment means 61 being disposed at a distinct side of the body of a user. The curvilinear upper back and shoulder contact means 63, disposed at each side of the body of a user, preferably comprises a tube 72, preferably of aluminum, a first cylindrical section of padding 66, preferably of "AP ARMAFLEX", and a second cylindrical section of padding 68, preferably of "AP ARMAFLEX". The first transverse attachment means 65, disposed at each side of the body of a user, preferably comprises a ninety degree (90°) tee 76, preferably of aluminum. The first transverse upper back contact means 67, (see FIG. 2), disposed across and in back of the body of a user, preferably comprises a tube 71, (see FIG. 4), preferably of aluminum, and a cylindrical section of padding 70, (see FIG. 4), preferably of "AP ARMAFLEX". The second transverse attachment means 69, disposed at each side of the body of a user, preferably comprises a ninety degree (90°) tee 74, preferably of aluminum. The second transverse upper back contact means 73, disposed across and in back of the body of a user, preferably comprises a tube 78, (see FIG. 5), preferably of aluminum, and a cylindrical section of padding 79, (see FIG. 5), preferably of "AP ARMAFLEX". The coupling means 75, disposed at each side of the body of a user, preferably comprises an adjustable coupler 80 and a set screw 82.

The fixed jaw slide 54 is attached at a first end to the eye end 20 in a manner allowing the rotation of the eye end 20 with respect to the fixed jaw slide 54, and is fixedly attached at a second end to a first end of the tube 72. The rotatable attachment is accomplished by the fastener 60 rotatably fastening the fixed jaw slide 54 to the eye end 20 (the necessity for such rotatable attachment being explained in the following paragraph). The fixed jaw slide 54 will not contact the body of a user at its lower surface if the head support device 10 fits properly, but will instead be in front of the body of a user. The fixed jaw slide 56 is fixedly attached to an interior portion of the tube 72, an aperture being provided through the fixed jaw slide 56 for this purpose. The fixed jaw slide 56 is attached to the eye end 62 in a manner allowing the rotation of the eye end 62 with respect to the fixed jaw slide 56. The rotatable attachment is accomplished by the fastener 58 rotatably fastening the fixed jaw slide 56 to the eye end 62 (the necessity for such rotatable attachment being explained in the following paragraph).

It will be appreciated that the angular adjustment of the upper section 12 will cause the tubes 22, 64 to rotate. The rotation of the tube 64 will, in turn, cause the eye end 62 to rotate with respect to the jaw slide 58, thus necessitating the previously mentioned rotatable attachment between the jaw slide 58 and the eye end 62. The rotation of the tube 64, in conjunction with the rotation of the tube 22, will, in addition, cause the eye end 25 to rotate with respect to jaw slide 24, thus necessitating the previously mentioned rotatable attachment between the jaw slide 24 and the eye end 25. The rotation of the tube 22 will, in turn, cause the eye end 20 to rotate with respect to the jaw slide 60, thus necessitating the previously mentioned rotatable attachment between the jaw slide 60 and the eye end 20.

The first cylindrical section of padding 66 covers the tube 72 for substantially all the length of the tube 72 between the fixed jaw slide 56 and the fixed jaw slide 54. The tube 72 is straight between the fixed jaw slides 54, 56. The tube 72 is curved between the fixed jaw slide 56 and the tee 76. The second cylindrical section of padding 68 covers the tube 72 for substantially all the length of the tube 72 between the fixed jaw slide 56 and the tee 76. Each of the tees 76 connects one of the tubes 72 to one end of the tube 71. The tube 71 is covered by the cylindrical section of padding 70 for substantially all of the length of the tube 71. Each of the tees 74 connect one of the tubes 72 to one end of the tube 78. The tube 78 is covered by the cylindrical section of padding 79 for substantially all of the length of the tube 78. The padding 66, 68, 70, 79 is designed to provide a padded contact between the head support device 10 and a user's upper back and shoulders so as to minimize user discomfort when wearing the device for extended periods of time. A padded contact is especially necessary since the force applied by a user's head to the head support section 32 of the head support device 10 is transmitted to the user's upper back and shoulders through the padding 66, 68, 70, 79 (see explanation below).

A second end of the tube 72 is attached to the adjustable coupler 80. The adjustable coupler 80 comprises a collar 83, preferably of "LEXAN", disposed at the second end of the tube 72 and a fastener 81, preferably of metal, passing through the collar 83 perpendicularly to the axis of the tube 72 and contacting the tube 72, thereby fixing the adjustable coupler 80 relative to the tube 72.

The lower section 16 comprises a belt means 101, a back conforming means 103, (see FIG. 2), and a belt connection means 90 (shown only schematically in FIG. 1). The belt means 101 preferably comprises a back support belt 84, (shown only schematically in FIGS. 1 and 2), which adjustably encircles the waist area of a user, and two shoulder loop straps 87, (not shown in FIGS. 1 and 2), for adjustably encircling the shoulders of a user. The back conforming means 103 preferably comprises two tube legs 86, preferably of aluminum, and two end caps 88, preferably of plastic, at the lower ends of and enclosing the tube legs 86. The belt connection means 90 connects the belt means 101 to the back conforming means 103 preferably by connecting the back support belt 84 to the tube legs 86.

The tube legs 86 are preferably vertically adjustable to fit in the small of a user's back without discomfort. The phantom outlines of the tube legs 86 and the end caps 88 on FIGS. 1 and 2 illustrate the vertical adjustment. The end caps 88 and the lower end of the tube legs 86 contact a user's lower back. The upper end of each of the tube legs 86 passes through each of the adjustable couplers 80 and each of the tubes 72. The set screw 82 is attached to the adjustable coupler 80 so that the axis of rotation of the set screw 82 is perpendicular to the axis of the tube leg 86. The set screw 82 is in contact with the tube leg 86 when the tube leg 86 is stationary, thus assuring the stationary position of the tube leg 86. When the set screw 82 is rotated in an appropriate direction, the set screw 82 is released from contact with the tube leg 86 and the tube leg 86 may be adjusted vertically for maximum comfort in conforming to the small of the user's back. The set screw 82 is preferably metallic, but the head of the set screw 82 is preferably covered with a plastic cap 27 (see FIG. 1b) to allow a user to turn the set screw 82 without the user's hands suffering injury or pain.

It should be appreciated that, alternatively, the tube legs 86 may be of a fixed length if the head support device 10 is custom made for a particular individual. In such a case, the set screw 82 would be preferably replaced by a fastener (not shown) contacting each tube leg 86 and fixing it in place.

Figure 6:
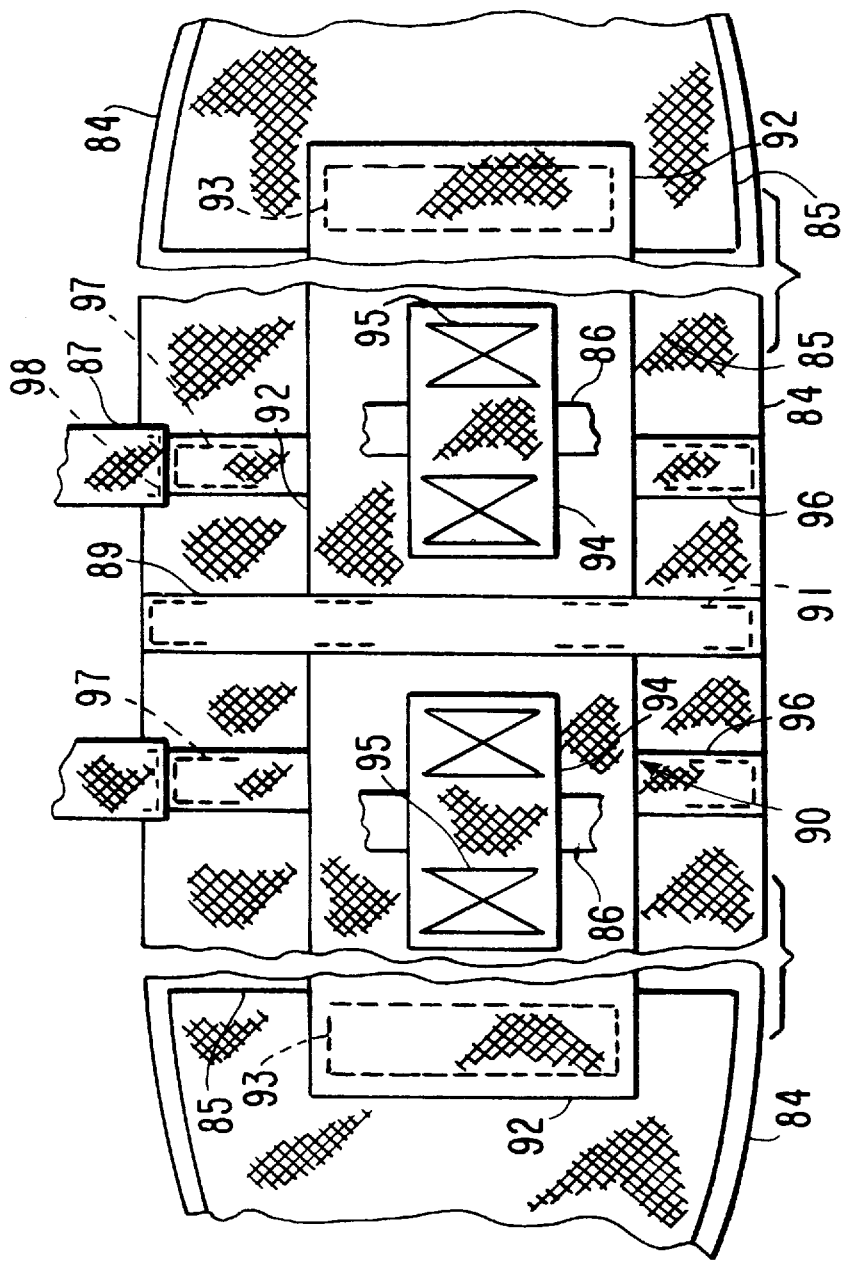
FIG. 6 is a partial rear elevational view looking in the direction of 6—6 in FIG. 1.

FIG. 6, taken as a partial elevational view of FIG. 1, shows the belt connection means 90 and its connection to the tube legs 86 and the back support belt 84 in greater detail. The belt connection means 90 comprises two looping pads 94, preferably of polypropylene, and one base pad 92. Each of the looping pads 94 form a loop over and enclose one of the tube legs 86. Each of the looping pads 94 is attached to the base pad 92 by x-shaped stitches 95. The belt connection means 90 is fixedly attached to the back support belt 84 by a connector strip 89 passing over the base pad 92 and stitched to the base pad 92 and the back support belt 84 by stitches 91. In addition, the belt connection means 90 is removably attached to the back support belt 84 by attachment surfaces 93, preferably of "VELCRO", on the base pad 92 and attachment surfaces 85, preferably of "VELCRO", on the back support belt 84. The removable attachment of the belt connection means 90 to the back support belt 84 allows the removal of the connection means 90 from looping engagement through the looping pads 94 with the tube legs 86. FIG. 6 also shows the attachment of the shoulder loop straps 87 to the back of the back support belt 84. The shoulder straps 87 are attached to the back support belt 84 by stitches 98 and reinforcing strips 96 are attached to the back support belt 84 by stitches 97 below the connection between the shoulder loop straps 87 and the back support belt 84 to give the back support belt 84 the strength needed at these connection points.

Figure 8:
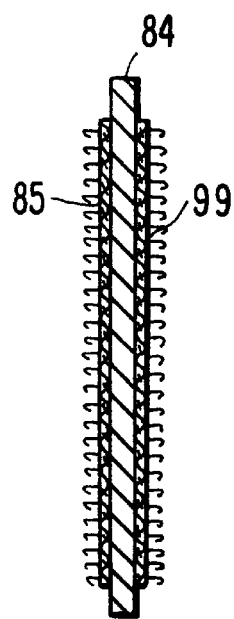
FIG. 8 is a cross-sectional view looking in the direction of 8—8 in FIG. 7.
Figure 7:
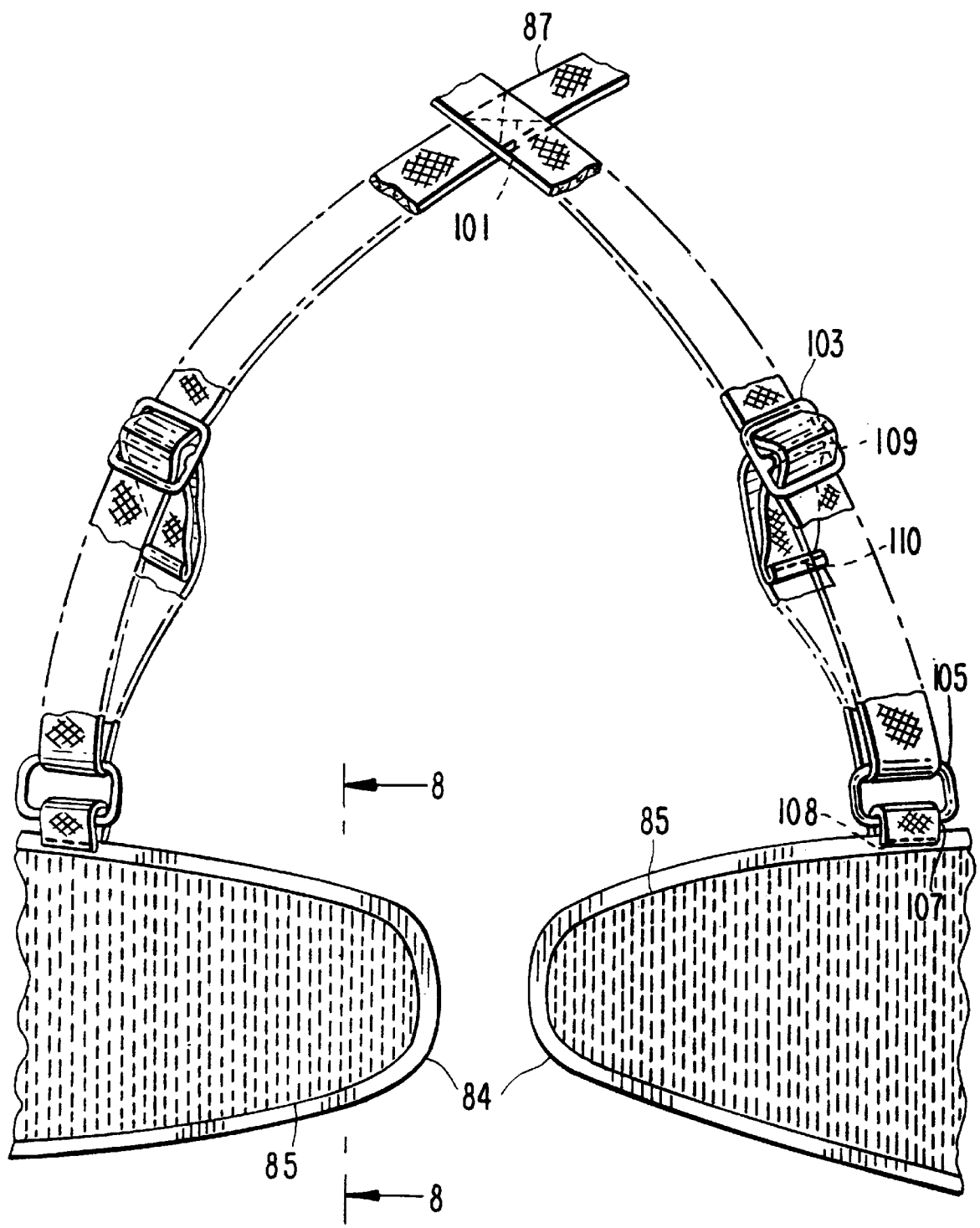
FIG. 7 is a partial front elevational view looking in the direction of 7—7 in FIG. 1.

FIG. 7, taken as a partial elevational view of FIG. 1, shows the shoulder strap loops 87 and their attachment to the front of the back support belt 84 in more detail. The shoulder strap loops 87 meet at a place in their interior in an x-shaped connection where one shoulder strap loop 87 passes over the other and is stitched to the other by stitches 101. Buckles 103 with three transverse bars are located on each side of a user's body to allow adjustment of the length of the shoulder strap loop 87 which passes through each of the buckles. One end of the shoulder strap loop 87 passes over the middle bar 109 of the buckle 103 and is fixedly attached to an interior portion of the shoulder strap loop 87 by stitches 110 to produce a fixed end, thereby allowing the length adjustment of the shoulder strap loop 87 by movement of the fixed end and the buckle 103 relative to a bottom buckle 105 over which the shoulder loop strap 87 passes. The bottom buckle 105 also serves to attach the shoulder loop strap 87 to the back support belt 84 by a connection loop 107 attached to the back support belt 84 by stitches 108. The two ends of the back support belt 84 are removably attached together in the front of a user's waist area by the attachment surfaces 85 and the attachment surface 99 (see FIG. 8), preferably of "VEL-CRO".

The belt connection means 90 and the back support belt 84 transmit a portion of the weight of the device 10 to a user's waist area. The shoulder strap loops 87 further distribute a portion of the weight to a user's shoulders. The back support belt 84 with the attachment surfaces 85, 99 attached, the back support belt 84 being connected to the shoulder strap loops 87 (the shoulder strap loops 87 having on them the buckles 103, 105) and being connected to the belt connection means 90, except for the looping pads 94, can be obtained from America's Choice, Los Angeles, Calif. 90037.

It should be understood that although the back support belt 84 is shown in the drawings and described above as being attached to the tube legs 86 by the belt connection means 90, the back support belt 84 may, alternatively, be attached to the tubes 72 through the belt connection means 90, depending on the height of a user relative to the head support device 10.

Although the support members of the device 10 have been described as aluminum tubes, any material having the strength and light weight qualities of aluminum such as high strength plastics or composite materials could be substituted for the aluminum. All of the "LEXAN" fittings, stainless steel tees, and aluminum tubing used in the head support device 10 can be obtained from Taco Metals, 50 NE 175th Street, Miami, Fla. 33162. Although as previously stated, aluminum is the preferred material for the tees, Applicant, to date has only been able to obtain stainless steel tees.

Figure 9:
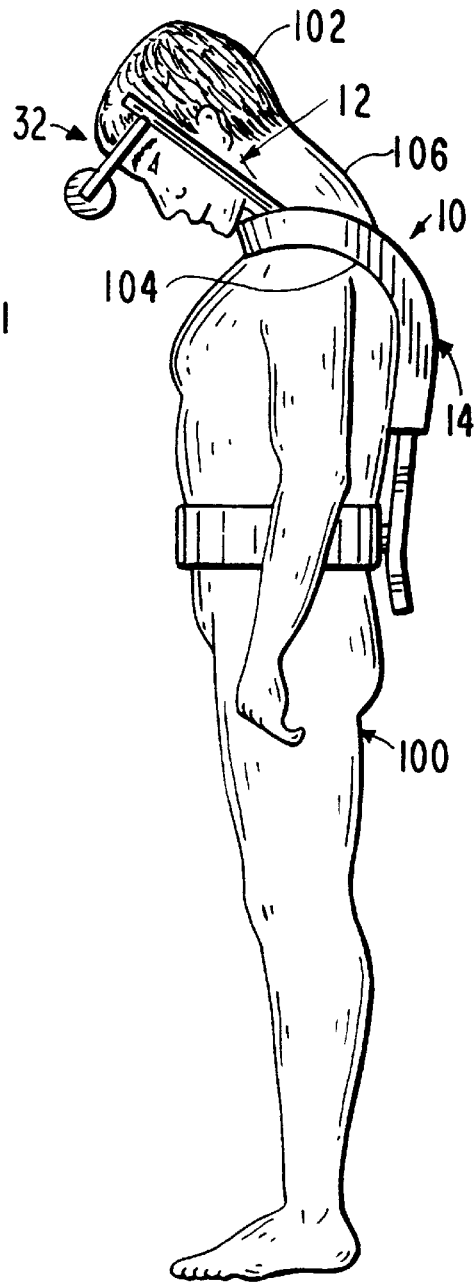
FIG. 9 is a schematic drawing showing a user wearing the head support device.

FIG. 9 schematically shows a user 100 with the head support device 10 on and demonstrates its method of operation. As shown in FIG. 9, the user's head 102 is at an arbitrary angle between an upright and a horizontal position and is supported by the head support section 32 of the head support device 10. The upper section 12 of the device 10 acts as a cantilever to transfer the force applied by the user's head 102 to the head support section 32 back to the intermediate section 14 of the head support device 10. The force applied by the user's head 102 is then transferred to the user's upper back and shoulders 104 by the intermediate section 14 of the device 10 through the padding 66, 68, 70, 79 which is in contact with the user's upper back and shoulders 104. This process of force transfer largely prevents the force applied to the device 10 by the user's head 102 from being transferred through the user's neck 106 which allows the user to keep his or her head 102 in the position shown for extended periods of time without the degree of inevitable neck strain that would result if the user's head 102 were placed in the position shown without the device 10 being on the user 100.

While preferred embodiments of the present invention have been described in detail, various modifications, alterations, and changes may be made without departing from the spirit and scope of the present invention as defined in the following claims. For example, it should be appreciated that the height of the head support device 10 will vary with the height of a user. Furthermore, the width of the head support device 10 will vary to accomodate the varying width between shoulders of various users.

What is claimed is:

1. A head support device which comprises:
    a. an angularly adjustable upper section adapted to support and restrain the head of a user at a selected angular position within a range of angular positions from a generally horizontal position to a generally vertical position;
    b. a fixed intermediate section connected to said angularly adjustable upper section and adapted to contact the shoulders and upper back of a user; and
    c. a lower section connected to said fixed intermediate section and adapted to contact the lower back of a user; wherein said angularly adjustable upper section comprises a head support means adapted to support the head of a user and further comprises, at each side of the head of a user:
        1. a support means adapted to transmit a portion of the force produced by a user's head resting against said angularly adjustable upper section to said fixed intermediate section;
        2. a first rotatably adjustable attachment means adapted to rotatably attach a first end of said support means to a first end of said fixed intermediate section;
        3. a fixable sliding means adapted to longitudinally slide along said support means and to fix the position of said fixable sliding means relative to said support means, thereby changing the position of said fixable sliding means relative to said support means;
        4. a rotatably adjustable support means adapted to rotatably support said support means;
        5. a second rotatably adjustable attachment means adapted to rotatably attach said fixable sliding means to a first end of said rotatably adjustable support means;
        6. a third rotatably adjustable attachment means adapted to rotatably attach a second end of said rotatably adjustable support means to an interior portion of said fixed intermediate section;
        7. a connection means adapted to fixedly connect to said connection means said head support means and to slidingly connect said connection means to said support means, thereby allowing said connection means to longitudinally slide along said support means to change the position of said connection means and said head support means relative to said support means; and
        8. a releasable head enclosing means attached to said connection means adapted to enclose the head of a user and releasably attached to the head enclosing means on the other side of the head of a user.

2. A head support device as claimed in claim 1, wherein said fixable sliding means comprise a first releasable position setting means adapted to releasably fix the position of said fixable sliding means relative to said support means and said connection means comprise a second releasable position setting means adapted to releasably fix the position of said connection means relative to said support means.

3. A head support device as claimed in claim 2, wherein said connection means further comprises a ninety degree tee.

4. A head support device as claimed in claim 1, wherein said first rotatably adjustable attachment means, said second rotatably adjustable attachment means, and said third rotatably adjustable attachment means each comprise:
    a. an eye end; and
    b. a fastener.

5. A head support device as claimed in claim 1, wherein said fixable sliding means comprises a jaw slide.

6. A head support device as claimed in claim 1, wherein said head support means comprises:
    a. two headrest support means, each of said headrest support means being disposed on each side of the head of a user, each of said headrest support means being adapted to attach at a first end to each of said connection means;

b. a headrest means adapted to permit a user to rest said user's head thereon, said headrest means spanning between said two headrest support means and being attached at each end to one of said two headrest support means; and c. headrest attachment means adapted to attach said headrest means to said two headrest support means.

7. A head support device as claimed in claim 6, wherein said headrest support means comprises an aluminum tube, said headrest means comprises:

a. a tube;

b. a cylindrical section of padding covering said tube; and c. a cylindrical section of removable padding covering said cylindrical section of padding;

and said headrest attachment means comprises:

a. a ninety degree tee; and b. a ninety degree elbow.

8. A head support device as claimed in claim 7, further comprising removable viewing means removably attached to said ninety degree tee and adapted to permit a user to view said user's surroundings, said removable viewing means comprising:

a. a hanger tube fitting within and removably attached to said ninety degree tee;

b. a collar attached to said hanger tube;

c. an arm adjustable in the vertical, horizontal, and angular directions and attached to said collar; and d. a mirror attached to said arm.

9. A head support device as claimed in claim 6, further comprising removable viewing means removably attached to said head support means and adapted to permit a user to view said user's surroundings.

10. A head support device as claimed in claim 1, wherein said fixed intermediate section comprises:

a. a first transverse upper back contact means running transversely and in back of a user's body, said first transverse upper back contact means being adapted to transfer a portion of said force produced by said user's head to said user's upper back; and b. a second transverse upper back contact means running transversely and in back of a user's body, said second transverse upper back contact means being adapted to transfer a portion of said force produced by said user's head to said user's upper back;

and further comprises, at each side of the body of a user corresponding to each side of the head of a user:

a. a first attachment means disposed at said first end of said fixed intermediate section adapted to attach to said first rotatably adjustable attachment means;

b. a second attachment means disposed at said interior portion of said fixed intermediate section adapted to attach to said third rotatably adjustable attachment means;

c. a curvilinear upper back and shoulder contact means which is attached at a first end to said first attachment means, is attached at an interior portion to said second attachment means, and is adapted to transfer a portion of said force produced by said user's head resting against said angularly adjustable upper section to said user's upper back and shoulders;

d. a first transverse attachment means adapted to attach said curvilinear upper back and shoulder contact means to said first transverse upper back contact means;

e. a second transverse attachment means adapted to attach said curvilinear upper back and shoulder contact means to said second transverse upper back contact means; and f. a coupling means disposed at a second end of said fixed intermediate section adapted to coupling a first end of said lower section to a second end of said curvilinear upper back and shoulder contact means.

11. A head support device as claimed in claim 10, wherein said first attachment means and said second attachment means each comprise a jaw slide and said first transverse attachment means and said second transverse attachment means each comprise a ninety degree tee.

12. A head support device as claimed in claim 10, wherein said curvilinear upper back and shoulder contact means comprises:

a. a tube;

b. a first cylindrical section of padding covering said tube and disposed between said first attachment means and said second attachment means; and c. a second cylindrical section of padding covering said tube and disposed between said first attachment means and said first transverse attachment means.

13. A head support device as claimed in claim 10, wherein said first transverse upper back contact means and said second transverse upper back contact means each comprise:

a. a tube; and b. a cylindrical section of padding covering said tube.

14. A head support device as claimed in claim 10, wherein said lower section comprises:

a. back conforming means, disposed at each side of a user's body corresponding to each side of a user's head, adapted to conform to the small of a user's back and attached at a first end to said coupling means;

b. a belt means adapted for adjustably encircling the waist area and the shoulders of a user; and c. a belt connection means adapted for connecting said belt means to said back conforming means.

15. A head support device as claimed in claim 14, wherein said back conforming means comprises a tube and an end cap adapted for enclosing a second end of said back conforming means.

16. A head support device as claimed in claim 14, wherein said belt connection means comprises looping pads removably enclosing said back conforming means and attached to the remainder of said belt connection means.

17. A head support device as claimed in claim 14, wherein said back conforming means are adjustably attached at a first end to said coupling means, said back conforming means being vertically adjustable with respect to the small of a user's back.

18. A head support device as claimed in claim 10, wherein said fixed intermediate section further comprises:

a. a belt means adapted for adjustably encircling the waist area and the shoulders of a user; and b. a belt connection means adapted for connecting said belt means to said curvilinear upper back and shoulder contact means.

19. A head support device as claimed in claim 18, wherein said lower section comprises back conforming means, disposed at each side of a user's body corresponding to each side of a user's head, adapted to conform to the small of a user's back and attached at a first end to said coupling means.

20. A head support device as claimed in claim 19, wherein said back conforming means are adjustably attached at a first end to said coupling means, said back conforming means being vertically adjustable with respect to the small of a user's back.

* * * * *